United States Patent
Pan et al.

(10) Patent No.: US 10,925,818 B2
(45) Date of Patent: Feb. 23, 2021

(54) ORAL CARE COMPOSITIONS AND METHODS FOR INCREASING STABILITY OF THE SAME

(71) Applicant: Colgate-Palmolive Company, New York, NY (US)

(72) Inventors: Guisheng Pan, Philadelphia, PA (US); Lin Fei, Kendall Park, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 85 days.

(21) Appl. No.: 15/827,758

(22) Filed: Nov. 30, 2017

(65) Prior Publication Data

US 2019/0159983 A1 May 30, 2019

(51) Int. Cl.
| | | |
|---|---|---|
| *A61K 8/22* | (2006.01) | |
| *A61K 8/24* | (2006.01) | |
| *A61Q 11/00* | (2006.01) | |
| *A61K 8/49* | (2006.01) | |

(52) U.S. Cl.
CPC .............. *A61K 8/24* (2013.01); *A61K 8/22* (2013.01); *A61K 8/4913* (2013.01); *A61Q 11/00* (2013.01); *A61K 2800/28* (2013.01); *A61K 2800/31* (2013.01); *A61K 2800/92* (2013.01)

(58) Field of Classification Search
CPC .......... A61K 8/4913; A61K 8/22; A61K 8/24; A61K 2800/28; A61K 2800/92; A61K 2800/31; A61Q 11/00
See application file for complete search history.

(56) References Cited

U.S. PATENT DOCUMENTS

| | | |
|---|---|---|
| 3,066,056 A | 11/1962 | Schlaeger et al. |
| 3,227,618 A * | 1/1966 | Manahan ................. A61K 8/21 424/52 |
| 3,577,521 A | 5/1971 | Scheller et al. |
| 4,024,239 A | 5/1977 | Pader |
| 4,582,701 A * | 4/1986 | Piechota, Jr. ............ A61K 8/25 424/52 |
| 6,511,654 B2 | 1/2003 | Ibsen et al. |
| 8,591,868 B2 | 11/2013 | Chopra et al. |
| 8,911,712 B2 | 12/2014 | Buelo et al. |
| 2007/0071695 A1 | 3/2007 | Beno et al. |
| 2017/0143599 A1 | 5/2017 | Fei et al. |

OTHER PUBLICATIONS

International Search Report and Written Opinion of the International Searching Authority in International Application No. PCT/2017/063957, dated May 9, 2018.

* cited by examiner

*Primary Examiner* — Lezah Roberts

(57) ABSTRACT

Anhydrous oral care compositions and methods for making and using the same are described herein. The anhydrous oral care compositions may include an orally acceptable vehicle, a peroxide whitening agent, and an abrasive system. The abrasive system may include at least one abrasive having a pellicle cleaning ratio (PCR) greater than or equal to 100.

8 Claims, No Drawings

ORAL CARE COMPOSITIONS AND METHODS FOR INCREASING STABILITY OF THE SAME

BACKGROUND

Conventional oral care products (e.g., toothpastes, whitening gels, whitening trays, etc.) and peroxide whitening agents thereof are often utilized to whiten teeth. For example, conventional whitening toothpastes including hydrogen peroxide are often utilized to oxidize chromophores bound to surfaces of teeth to thereby whiten the teeth. While whitening toothpastes including hydrogen peroxide have proven to be effective for whitening teeth, the peroxides are often unstable (e.g., reactive) and subject to degradation or reactivity with other components of the toothpastes. For example, the hydrogen peroxide in whitening toothpastes are often highly reactive to conventional abrasives, such as sodium metaphosphate and dicalcium phosphate hydrate, thereby reducing the whitening efficacy of the toothpastes.

In view of the foregoing, conventional oral care products are often provided as a two-component whitening system to separate the hydrogen peroxide from potentially reactive components until the time of use when they may be mixed. While conventional two-component whitening systems have been able to prevent reactivity between the hydrogen peroxide and other components of the toothpastes, the implementation of these two-component whitening systems are cost-prohibitive. Further, the two-component whitening systems may often exhibit decreased mixing efficiency, which results in heterogeneous mixtures.

What is needed, then, are improved single phase oral care compositions including peroxide whitening agents having increased peroxide stability.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Embodiments of the disclosure may provide an anhydrous oral care composition including an orally acceptable vehicle, a peroxide whitening agent, and an abrasive system. The abrasive system may include at least one abrasive having a pellicle cleaning ratio (PCR) greater than or equal to 100.

In at least one embodiment, the abrasive system may further include an abrasive having a PCR less than or equal to 85.

In at least one embodiment, the abrasive having a PCR less than or equal to 85 may be sodium metaphosphate.

In at least one embodiment, the abrasive having a PCR greater than or equal to 100 may be anhydrous dicalcium phosphate.

In at least one embodiment, the abrasive system may consist essentially of sodium metaphosphate and anhydrous dicalcium phosphate.

In at least one embodiment, the abrasive system may consist of sodium metaphosphate and anhydrous dicalcium phosphate.

In at least one embodiment, the abrasives may be present in an amount of from about 18 weight % to about 22 weight %, preferably about 19 weight % to about 21 weight %, or more preferably about 20 weight %, based on a total weight of the oral care composition.

In at least one embodiment, a weight ratio of the sodium metaphosphate to the anhydrous dicalcium phosphate may be from about 2.8:1 to about 3.4:1, preferably about 3:1 to about 3.2:1, or more preferably about 2.9:1 to about 3.1:1.

In at least one embodiment, the peroxide whitening agent may include a source of hydrogen peroxide, preferably the source of hydrogen peroxide is a cross-linked polyvinylpyrrolidone (PVP) hydrogen peroxide complex.

Embodiments of the disclosure may provide a method for whitening teeth. The method may include contacting any one of the anhydrous oral care composition disclosed herein with surfaces of the teeth.

Embodiments of the disclosure may further provide a method for increasing hydrogen peroxide stability in an anhydrous oral care composition. The method may include combining a peroxide whitening agent with an abrasive system, where the abrasive system includes at least one abrasive having a pellicle cleaning ratio (PCR) greater than or equal to 100.

In at least one embodiment, the abrasive system may further include an abrasive having a PCR less than or equal to 85.

In at least one embodiment, the abrasive having a PCR less than or equal to 85 may be sodium metaphosphate.

In at least one embodiment, the abrasive having a PCR greater than or equal to 100 may be anhydrous dicalcium phosphate.

In at least one embodiment, the abrasive system may consist essentially of sodium metaphosphate and anhydrous dicalcium phosphate.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that oral care products and/or oral care compositions thereof that include an abrasive system having an anhydrous dicalcium phosphate exhibited stability with hydrogen peroxide. It was also surprisingly and unexpectedly discovered that anhydrous dicalcium phosphate exhibited both stability with hydrogen peroxide and improved stain removal capability or PCR values as compared to a conventional abrasive (e.g., calcium pyrophosphate). It was further surprisingly and unexpectedly discovered that a combination or mixture of the anhydrous dicalcium phosphate and sodium metaphosphate, which exhibits a relatively lower PCR value, exhibited both stability with hydrogen peroxide and a relatively greater PCR value or stain removal capability than conventional abrasives alone (e.g., calcium pyrophosphate, sodium metaphosphate alone, dicalcium phosphate hydrate, etc.).

Compositions disclosed herein may be or include an oral care product and/or an oral care composition thereof. The oral care composition may be a non-aqueous oral care composition, such as a non-aqueous dentifrice or toothpaste. The oral care composition may include a peroxide whitening agent and an abrasive system. The abrasive system may include a single abrasive or a mixture or combination of abrasive. The abrasive system may include an abrasive having a relatively high pellicle cleaning ratio (PCR) (e.g., PCR>110, 115, or 120). The abrasive system may also include a combination or mixture of at least one abrasive having a relatively low PCR (e.g., PCR<80 or <75) and an additional abrasive. The abrasive system may further include an abrasive having a relatively high pellicle cleaning ratio (PCR) (e.g., PCR>110, 115, or 120) and an abrasive having a relatively low PCR (e.g., PCR<80 or <75). In at least one implementation, the abrasive system may include a combination or mixture of sodium metaphosphate and calcium pyrophosphate. In another implementation, the abrasive system may include a combination or mixture of sodium metaphosphate and anhydrous dicalcium phosphate. In yet another implementation, the abrasive system may include a single abrasive, such as anhydrous dicalcium phosphate.

The oral care composition prior to use may be anhydrous. For example, the oral care composition may be free or substantially free of water. As used herein, "free of water" or "substantially free of water" may refer to a composition that contains water in an amount of less than 5.0 weight %, less than 3.0 weight %, less than 1.0 weight %, less than 0.1 weight %, less than 0.05 weight %, less than 0.01 weight %, less than 0.005 weight %, or less than 0.0001 weight %, based on a total weight of the oral care composition. The oral care composition prior to use may have a "low water content". As used herein, "low water content" may refer to a composition that contains water in an amount greater than about 5 weight % and less than about 7 weight % or less than about 10 weight %.

The oral care product or the oral care composition thereof may be a single phase oral care product or single phase oral care composition. For example, all the components of the oral care product or the oral care composition thereof may be maintained together with one another in a single phase and/or vessel. For example, the all the components of the oral care product or the oral care composition thereof may be maintained in a single phase, such as a single homogenous phase. The single homogenous may be an anhydrous formulation or an anhydrous composition.

The oral care composition may form at least a portion of or be used in one or more oral care products. The oral care composition may include or be combined with an orally acceptable vehicle to form the oral care product (e.g., the toothpaste). Illustrative oral care products may include, but are not limited to, a toothpaste (dentifrice), a prophylactic paste, a tooth powder, a tooth polish, a tooth gel (e.g., a whitening gel), a chewing gum, a lozenge, a mouthwash, a whitening strip, a paint-on gel, varnish, veneer, and tube, syringe or dental tray comprising a gel or paste, or a gel or paste coated on an application support such as dental floss or a toothbrush (e.g., a manual, electric, sound, a combination thereof or ultrasound toothbrush). In a typical implementation, the oral care composition may be or may form at least a portion of a toothpaste.

In at least one implementation, the orally acceptable vehicle may include one or more humectants. Illustrative humectants may be or include, but are not limited to, glycerin, propylene glycol, polyethylene glycol, and combinations thereof. In a preferred implementation, the orally acceptable vehicle may be or include, but is not limited to, propylene glycol. The propylene glycol may be present in an amount of from 5 weight % to about 60 weight %, based on a total weight of the oral care composition. For example, the propylene glycol may be present in an amount of from about 5 weight %, about 10 weight %, about 15 weight %, or about 20 weight % to about 25 weight %, about 30 weight %, about 35 weight %, about 40 weight %, about 45 weight %, about 50 weight %, about 55 weight %, or about 60 weight %. In another example, the propylene glycol may be present in an amount of from about 5 weight % to about 60 weight %, about 10 weight % to about 55 weight %, about 15 weight % to about 50 weight %, about 20 weight % to about 25 weight %, about 20 weight % to about 40 weight %, about 20 weight % to about 35 weight %, about 20 weight % to about 30 weight %, or about 20 weight % to about 25 weight %. In an exemplary implementation, the propylene glycol may be present in an amount of about 20 weight % to about 30 weight %, preferably about 20 weight % to about 25 weight %, and more preferably about 22 weight % to about 25 weight %. In a preferred implementation, the propylene glycol may be present in an amount of about 22 weight % to about 25 weight % or about 23 weight %.

The oral care product or the composition thereof may include one or more peroxide whitening agents. The peroxide whitening agents may be or include, but are not limited to, hydrogen peroxide or one or more sources of hydrogen peroxide. For example, the peroxide whitening agents may be hydrogen peroxide and/or hydrogen peroxide releasing substances. The one or more sources of hydrogen peroxide may be or include any compound or material configured to release hydrogen peroxide. Preferably, the peroxide whitening agents include, but are not limited to, solid peroxide whitening agents and bound peroxide whitening agents which are substantially anhydrous oxygen generating compounds. Solid peroxide whitening agents may include, but are not limited to, peroxides and persulfates. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include, but are not limited to, lithium peroxide, potassium peroxide, sodium peroxide, magnesium peroxide, calcium peroxide, barium peroxide, and mixtures thereof. Organic peroxy compounds include, but are not limited to, urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include, but are not limited to, organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. The peroxide whitening agents may be preferably bound. For example, peroxide may be bound to a polymer such as PVP (poly(N-vinylpyrrolidone). Suitable PVP complexes are disclosed, for example, in U.S. Pat. No. 5,122,370, the contents of which are incorporated herein by reference. In some implementations, it may be desirable to use any known peroxide whitening agent except sodium percarbonate and/or any of the percarbonate salts. The sources of hydrogen peroxide or peroxide whitening agents may also be or include, but are not limited to, PEROXYDONE™ XL 10 complex or POLYPLASDONE® XL 10F, which are commercially available from Ashland Inc. of Covington, Ky. In a typical implementation, the source of hydrogen peroxide includes a cross-linked PVP hydrogen peroxide complex.

The amount or concentration of the source of hydrogen peroxide may vary widely. In at least one example, the source of hydrogen peroxide may be present in an amount that provides a concentration of hydrogen peroxide of less than or equal to 4 weight %, less than or equal to 3.5 weight %, less than or equal to 3 weight %, less than or equal to 2.5 weight %, less than or equal to 2 weight %, or less than or equal to 1.5 weight %, based on a total weight of the oral care product or the composition thereof. In at least one implementation, the source of hydrogen peroxide may be present in an amount greater than or equal to 1 weight % and less than or equal to 30 weight %, based on a total weight of the oral care composition. For example, the source of hydrogen peroxide may be present in an amount of from about 1 weight %, about 3 weight %, about 5 weight %, about 7 weight %, about 9 weight %, about 11 weight %, about 13 weight %, or about 15 weight % to about 17 weight %, about 19 weight %, about 21 weight %, about 23 weight %, about 25 weight %, about 27 weight %, about 29 weight %, or about 30 weight %. In another example, the source of hydrogen peroxide may be present in an amount of from about 1 weight % to about 30 weight %, about 3 weight % to about 29 weight %, about 5 weight % to about 27 weight %, about 7 weight % to about 25 weight %, about 9 weight % to about 23 weight %, about 11 weight % to about 21 weight %, about 13 weight % to about 19 weight %, or about 15 weight % to about 17 weight %. In a preferred implementation, the source of hydrogen peroxide is a cross-linked PVP complexed with hydrogen peroxide, and is present in an amount of from about 8 weight % to about 14 weight %, preferably about 10 weight % to about 12 weight %, and more preferably about 11 weight %.

The oral care product or the composition thereof may include an abrasive system including one or more abrasives. As used herein, the term "abrasive" may also refer to materials commonly referred to as "polishing agents". Illustrative abrasives may include, but are not limited to, phosphate salts (e.g., insoluble phosphate salts), such as sodium metaphosphate, potassium metaphosphate, calcium pyrophosphate, magnesium orthophosphate, trimagnesium orthophosphate, tricalcium phosphate, dicalcium phosphate dihydrate, anhydrous dicalcium phosphate and the like. Other illustrative abrasives that may be included in the oral care product or the composition thereof may include, but are not limited to, calcium carbonate, magnesium carbonate, hydrated alumina, silica, zirconium silicate, aluminum silicate including calcined aluminum silicate, polymethyl methacrylate, and the like, and mixtures or combinations thereof. In at least one implementation, the abrasive system may be free or substantially free of hydrated phosphate salts, including, but not limited to, dicalcium phosphate dihydrate.

Illustrative abrasives may also be or include, but are not limited to, those previously considered to be incompatible in a peroxide containing formulation ("a peroxide-incompatible abrasive"). As used herein, "a peroxide-incompatible abrasive" may refer to an abrasive that substantially reacts with peroxides (e.g., hydrogen peroxide) so as to reduce a whitening efficacy of the medium. The reaction between the peroxides and the peroxide-incompatible abrasive may be in an aqueous medium (e.g., solution) or an anhydrous medium. "A peroxide-incompatible abrasive" may also refer to an abrasive that reacts with peroxides (e.g., hydrogen peroxide) in a single phase oral care composition (e.g., toothpaste) such that the amount of hydrogen peroxide present in the oral care composition after exposure to accelerated aging conditions for a period of 1, 2, 3, 4, 5, 10, 15, or 20 weeks is reduced by at least 0.5%, at least 0.6%, at least 0.7%, at least 0.8%, at least 0.9%, at least 1.0%, at least 1.1%, at least 1.2%, at least 1.3%, at least 1.4%, at least 1.5%, at least 1.6%, at least 1.7%, at least 1.8%, at least 1.9%, at least 2.0%, at least 2.5%, at least 3.0%, at least 3.5%, at least 4.0%, at least 4.5%, at least 5.0%, at least 5.5%, at least 6.0%, at least 6.5%, at least 7.00, at least 7.5%, at least 8.0%, at least 8.5%, at least 9.0%, at least 9.5%, at least 10.0%, at least 10.5%, at least 11.0%, at least 11.5%, at least 12.0%, at least 12.5%, at least 13.0%, at least 13.5%, at least 14.0%, at least 14.5%, at least 15%, at least 20%, at least 25%, or at least 30%. Illustrative "peroxide-incompatible abrasives" may be or include, but are not limited to, silica, calcium carbonate, hydroxyapatite, calcium phosphate, and the like.

In at least one implementation, one or more of the abrasives in the abrasive system may have a relatively high pellicle cleaning ratio (PCR) (e.g., PCR>110, 115, or 120). As used herein, an abrasive having a relatively high PCR may refer to an abrasive having a PCR of from about 100, about 105, about 110, about 115, about 118, about 119, or about 120 to about 121, about 123, about 125, about 130, about 135, about 140, or greater. For example, the abrasive having a relatively high PCR may refer to an abrasive having a PCR greater than or equal to 100, greater than or equal to 102, greater than or equal to 104, greater than or equal to 106, greater than or equal to 108, greater than or equal to 110, greater than or equal to 112, greater than or equal to 114, greater than or equal to 116, greater than or equal to 118, greater than or equal to 120, greater than or equal to 122, greater than or equal to 124, greater than or equal to 126, greater than or equal to 128, or greater than or equal to 130.

In at least one implementation, one or more of the abrasives in the abrasive system may have a relatively lower pellicle cleaning ratio (PCR). As used herein, an abrasive having a relatively low PCR may refer to an abrasive having a PCR of from about 10, about 20, about 30, about 40, about 50, or about 60 to about 90, about 89, about 88, about 87, about 86, about 85, about 84, about 83, about 82, about 81, about 80, about 79, about 78, about 77, about 76, about 75, about 74, about 73, about 72, about 71, or about 70. For example, the abrasive having a relatively low PCR may refer to an abrasive having a PCR less than or equal to 90, less than or equal to 89, less than or equal to 88, less than or equal to 87, less than or equal to 86, less than or equal to 85, less than or equal to 84, less than or equal to 83, less than or equal to 82, less than or equal to 81, less than or equal to 80, less than or equal to 79, less than or equal to 78, less than or equal to 77, less than or equal to 76, less than or equal to 75, less than or equal to 74, less than or equal to 73, less than or equal to 72, less than or equal to 71, or less than or equal to 70.

In a preferred implementation, the abrasive system includes a mixture or combination of at least two abrasives. For example, the abrasive system may include a combination or mixture of at least one abrasive having a relatively low pellicle cleaning ratio (PCR) and an additional abrasive. In another example, the abrasive system may include a combination or mixture of at least one peroxide-incompatible abrasive having a relatively high PCR and an additional abrasive. In yet another example, the abrasive system may include a combination or mixture of at least one abrasive having a relatively low pellicle cleaning ratio (PCR) and an abrasive having a relatively high PCR.

In an exemplary implementation, the abrasive system includes a mixture or combination of sodium metaphosphate and an additional abrasive. For example, the abrasive system may include a mixture or combination of sodium metaphosphate and calcium pyrophosphate. In another example, the abrasive system may include a mixture or combination of sodium metaphosphate and anhydrous dicalcium phosphate.

The amount or concentration of the abrasive system and abrasives thereof may vary widely. In at least one implementation, the amount or concentration of the abrasives may be from greater than 0 weight % to about 40 weight %, based on a total weight of the oral care product or the composition thereof. For example, the amount of the abrasives present in the oral care composition may be from greater than 0 weight %, about 2 weight %, about 4 weight %, about 6 weight %, about 8 weight %, about 10 weight %, about 12 weight %, about 14 weight %, about 16 weight %, about 18 weight %, or about 19 weight % to about 21 weight %, about 22 weight %, about 24 weight %, about 26 weight %, about 28 weight %, about 30 weight %, about 32 weight %, about 34 weight %, about 36 weight %, about 38 weight %, or about 40 weight %. In another example, the amount of the abrasives present in the oral care composition may be from greater than 0 weight % to about 40 weight %, about 2 weight % to about 38 weight %, about 4 weight % to about 36 weight %, about 6 weight % to about 34 weight %, about 8 weight % to about 32 weight %, about 10 weight % to about 30 weight %, about 12 weight % to about 28 weight %, about 14 weight % to about 26 weight %, about 16 weight % to about 24 weight %, about 18 weight % to about 22 weight %, or about 19 weight % to about 21 weight %. In a preferred implementation, the amount of the abrasives present in the oral care composition may be from about 18 weight % to about 22 weight %, preferably about 19 weight % to about 21 weight %, or more preferably about 20 weight %, based on a total weight of the oral care product or the composition thereof.

At discussed above, the abrasive system may include a mixture or combination of one or more abrasives. The weight ratio of a first abrasive to a second abrasive may vary widely. In at least one implementation, the weight ratio of the first abrasive to the second abrasive may be greater than or equal to about 0.2:1 and less than or equal to about 6:1. For example, the weight ratio of the first abrasive to the second abrasive may be from about 0.2:1, about 0.4:1, about 0.6:1, about 0.8:1, about 1:1, about 1.2:1, about 1.4:1, about 1.6:1, about 1.8:1, about 2:1, about 2.2:1, about 2.4:1, about 2.6:1, about 2.8:1, or about 3:1 to about 3.2:1, about 3.4:1 about 3.6:1, about 3.8:1, about 4:1, about 4.2:1, about 4.4:1, about 4.6:1, about 4.8:1, about 5:1, about 5.2:1, about 5.4:1, about 5.6:1, about 5.8:1, or about 6:1. In another example, the weight ratio of the first abrasive to the second abrasive may be from about 0.2:1 to about 6:1, about 0.4:1 to about 5.8:1, about 0.6:1 to about 5.6:1, about 0.8:1 to about 5.4:1, about 1:1 to about 5.2:1, about 1.2:1 to about 5:1, about 1.4:1 to about 4.8:1, about 1.6:1 to about 4.6:1, about 1.8:1 to about 4.4:1, about 2:1 to about 4.2:1, about 2.2: to about 4:1, about 2.4:1 to about 3.8:1, about 2.6:1 to about 3.6:1, about 2.8:1 to about 3.4:1, about 3:1 to about 3.2:1, or about 3:1. In an exemplary implementation, the weight ratio of the first abrasive to the second abrasive may be from about 2.9:1 to about 3.1:1, preferably about 3:1.

In at least one implementation, the oral care products and/or the oral care composition thereof may be free or substantially free of fluoride (e.g., soluble fluoride salts). In another implementation, the oral care products and/or the oral care composition thereof may further include fluoride, such as one or more fluoride ion sources (e.g., soluble fluoride salts). A wide variety of fluoride ion-yielding materials may be employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference. Illustrative fluoride ion sources include, but are not limited to, fluoride, stannous fluoride, sodium fluoride, potassium fluoride, sodium monofluorophosphate, fluorosilicate salts, such as sodium fluorosilicate and ammonium fluorosilicate, amine fluoride, ammonium fluoride, and combinations thereof. In a typical implementation, the fluoride ion source includes sodium monofluorophosphate. The amount of the fluoride ion source in the oral care composition may be greater than 0 weight % and less than 0.8 wt %, less than 0.7 wt %, less than 0.6 wt %, less than 0.5 wt %, or less than 0.4 wt %. The fluoride ion sources may be present in an amount sufficient to provide a total of about 100 to about 20,000 ppm, about 200 to about 5,000 ppm, or about 500 to about 2,500 ppm fluoride ions.

It should be appreciated to one having ordinary skill in the art, that the oral care products and/or the oral care composition thereof may include other additional ingredients/components. For example, the oral care products and/or the oral care composition thereof may include anti-caries agents, desensitizing agents, viscosity modifiers, diluents, pH modifying agents, humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

In at least one implementation, the additional ingredients/components may include one or more active materials configured to prevent and/or treat one or more conditions and/or disorders of the oral cavity. For example, the one or more active materials may be configured to prevent and/or treat one or more conditions and/or disorders of hard and/or soft tissue of the oral cavity. The active materials may also be configured to prevent and/or treat one or more physiological disorders and/or conditions, and/or provide a cosmetic benefit to the oral cavity.

In at least one implementation, the oral care products or the oral care composition thereof may include an anticalculus agent. Generally, anticalculus agents may not be compatible with some oral care composition, however, implementations of the present disclosure may incorporate anticalculus agents and the oral care composition into a single phase oral care product. Illustrative anticalculus agents may include, but are not limited to, phosphates and polyphosphates (e.g., pyrophosphates), polyaminopropanesulfonic acid (AMPS), hexametaphosphate salts, zinc citrate trihydrate, polypeptides, polyolefin sulfonates, polyolefin phosphates, diphosphonates. In a typical implementation, the anticalculus agents includes tetrasodium pyrophosphate (TSPP), sodium tripolyphosphate (STPP), or a combination thereof.

The oral care products or the oral care composition thereof may include an antioxidant. Any orally acceptable antioxidant may be used, including, but not limited to, butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and the like, and combinations and mixtures thereof.

The oral care product or the compositions thereof may have a pellicle cleaning ratio (PCR) of greater than 80, greater than 82, greater than 84, greater than 86, greater than 88, greater than 90, greater than 92, greater than 94, greater than 96, greater than 98, greater than 100, greater than 102, greater than 104, greater than 106, greater than 108, greater than 110, greater than 112, greater than 114, greater than 116, greater than 118, greater than 120, greater than 122, greater than 124, greater than 126, greater than 128, or greater than 130. In a preferred implementation, the oral care product or the compositions thereof may have a pellicle cleaning ratio (PCR) of greater than 100 and less than 120, preferably greater than 105 and less than 115, more preferably greater than 105 and less than 110.

The present disclosure may provide methods for increasing peroxide stability in an oral care product and the oral care composition thereof. The method may include at least partially preventing the peroxide whitening agent or peroxides from reacting with other components (e.g., abrasives) of the oral care composition under accelerated aging conditions (e.g., temperature from about 40° C. to about 50° C.). The method may also include at least partially preventing the peroxide whitening agent or peroxides from reacting with other components of the oral care composition for at least three months under accelerated aging conditions. The method may further include maintaining viability, stability, and/or compatibility with the peroxide whitening agent under accelerated aging conditions. For example, the method may include maintaining viability, stability, and/or compatibility with the peroxide whitening agent for at least three months.

It should be appreciated that all ingredients for use in the compositions described herein are orally acceptable. As used herein, the expression "orally acceptable" may define an ingredient that is present in a composition as described in an amount and form that does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

Five oral care compositions (1)-(5) including varying abrasives were evaluated for their reactivity, stability, and/or compatibility with hydrogen peroxide. The oral care compositions (1)-(5) were prepared by combining the ingredients/components according to Table 1. It should be appreciated that each of the oral care compositions (1)-(5) contained 3 weight % of hydrogen peroxide as provided by a cross-lined PVP complexed with hydrogen peroxide.

TABLE 1

Oral Care Compositions (1)-(5)

| Ingredient | (1) | (2) | (3) | (4) | (5) |
| --- | --- | --- | --- | --- | --- |
| Calcium Pyrophosphate ($Ca_2P_2O_7$) | 15.0 | — | — | — | — |
| Sodium Metaphosphate ($Na_6(PO_3)_6$) | — | 15.0 | — | — | 15.0 |
| Dicalcium Phosphate Hydrate ($CaHPO_4 \cdot 2H_2O$) | — | — | 15.0 | — | — |
| Anhydrous Dicalcium Phosphate ($CaHPO_4$) | — | — | — | 15.0 | 5.0 |
| Cross-linked PVP complexed with hydrogen peroxide | 16.5 | 16.5 | 16.5 | 16.5 | 16.5 |
| Excipients (Orally Acceptable Vehicle, Thickener, Viscosity Control Agent, Polymer, Anticalculus and/or Anti-tartar agent, Fluoride Ion Source, Flavor, Surfactants, Sweeteners, Fluoride, Antioxidants, Anticalculus and Tartar Control Agents, Polymers) | Q.S. | Q.S. | Q.S. | Q.S. | Q.S. |
| Total | 100 | 100 | 100 | 100 | 100 |

The stability of the oral care compositions (1)-(5) were evaluated under accelerated aging conditions. Particularly, each of the oral care compositions (1)-(5) were aged in an incubator maintained at 49° C. and 75% Relative Humidity (RH) for 2 months. To test the stability via bloating, each of the oral care compositions (1)-(5) were disposed in a standard crimped dentifrice tube. Each of the tubes were marked approximately 40 mm from the bottom of a crimp of the tube to indicate the point of measurement. Measurements of the bloating were conducted by measuring the respective width of each of the tubes with a digital caliper positioned at the point of measurement and at an angle parallel to the crimp of the tube. The results of the stability of the oral care compositions are summarized in Table 2.

TABLE 2

| Bloating of Oral Care Compositions (1)-(3) After Aging at 40° C. After 16 Weeks | | | | | |
|---|---|---|---|---|---|
| | (1) | (2) | (3) | (4) | (5) |
| Change in Bloating After 16 Wks (mm) | 10.00 | 2.78 | Burst after 24 hrs | 11.08 | 5.47 |

As indicated in Table 2, oral care composition (2), which included sodium metaphosphate as the abrasive exhibited lower reactivity with hydrogen peroxide as compared to calcium pyrophosphate, which was utilized in oral care composition (1). Table 2 also indicated that dicalcium phosphate hydrate was incompatible with hydrogen peroxide. It was surprisingly and unexpectedly discovered, however, that anhydrous dicalcium phosphate exhibited stability with hydrogen peroxide. Particularly, it was discovered that the anhydrous dicalcium phosphate exhibited similar stability as calcium pyrophosphate. This was particularly surprising because the hydrated form was previously found to be incompatible with hydrogen peroxide in oral care compositions.

To further compare the stability of the anhydrous dicalcium phosphate with the hydrated dicalcium phosphate, an oral care composition was prepared where anhydrous dicalcium phosphate was combined as discussed above with composition (4) of Table 1. Water in an amount equivalent to the amount of bound water contained in the dicalcium phosphate hydrate of composition (3) of Table 1 was then added to the anhydrous dicalcium phosphate formulation. Accordingly, a comparison of the dicalcium phosphate with bound water (i.e., hydrated dicalcium phosphate) and with free water (i.e., anhydrous dicalcium phosphate and added water) was performed. It should be appreciated that the composition including free water and anhydrous dicalcium phosphate were stable for an extended period of time, and exhibited relatively greater stability with peroxide than the hydrated dicalcium phosphate, which ruptured the dentifrice tube within the first 24 hours of preparing the composition. Accordingly, it is surprisingly and unexpectedly discovered that the anhydrous dicalcium phosphate exhibit relatively greater stability with the peroxide in the oral care compositions.

Example 2

The pellicle cleaning ratio (PCR) of the oral care compositions (1)-(5) of Example 1 were evaluated. It should be appreciated that the PCR is a measure of the cleaning characteristics of a dentifrice with values of from about 40 to about 200, and preferably values of from about 60 to about 200. The PCR values were determined according to the methods detailed and discussed in "In Vitro Removal of Stain with Dentifrice," G. K. Stookey, et al., *J. Dental Res.*, 61, 1236-9, 1982, the contents of which are incorporated herein by reference. The results of the PCR analysis are summarized in Table 3.

TABLE 3

| Pellicle Cleaning Ratio (PCR) Scores of Oral Care Compositions (1)-(5) | | | | | |
|---|---|---|---|---|---|
| | (1) | (2) | (3) | (4) | (5) |
| PCR | 95 | 82 | 57 | 119 | 107 |

As illustrated in Table 3, the oral care composition (2), which utilized sodium metaphosphate exhibited a relatively lower PCR value as compared to oral care composition (1), which utilized calcium pyrophosphate. This indicated that the oral care composition (2), which utilized sodium metaphosphate, had a relatively lower stain removal capability as compared to oral care composition (1), which utilized the calcium pyrophosphate. It was surprisingly and unexpectedly discovered, however, that the anhydrous dicalcium phosphate exhibited both stability with hydrogen peroxide, as discussed above, and improved stain removal capability or PCR values as compared to calcium pyrophosphate. It was further surprisingly and unexpectedly discovered that a combination or mixture of the anhydrous dicalcium phosphate and sodium metaphosphate, which was previously found to be incompatible with hydrogen peroxide, exhibited both stability with hydrogen peroxide and a relatively greater PCR value or stain removal capability.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An anhydrous oral care composition, comprising:
   an orally acceptable vehicle;
   a peroxide whitening agent comprising a source of hydrogen peroxide, which source of hydrogen peroxide is a cross-linked polyvinylpyrrolidone (PVP) hydrogen peroxide complex; and
   an abrasive system, wherein the abrasive system comprises anhydrous dicalcium phosphate and sodium metaphosphate, wherein the abrasive system is present in an amount of from about 18 weight % to about 22 weight %, based on a total weight of the oral care composition; and wherein the weight ratio of the sodium metaphosphate to the anhydrous dicalcium phosphate is from about 2.8:1 to about 3.4:1.

2. The anhydrous oral care composition according to claim 1, wherein the abrasive system consists essentially of sodium metaphosphate and anhydrous dicalcium phosphate.

3. The anhydrous oral care composition according to claim 1, wherein the abrasive system consists of sodium metaphosphate and anhydrous dicalcium phosphate.

4. A method for whitening teeth, comprising contacting a tooth surface of a subject in need thereof, with the anhydrous oral care composition according to claim 1.

5. The anhydrous oral care composition according to claim 1, wherein the abrasive system is present in an amount of about 19 weight % to about 21 weight %.

6. The anhydrous oral care composition according to claim 1, wherein the abrasive system is present in an amount of about 20 weight %, based on a total weight of the oral care composition.

7. The anhydrous oral care composition according to claim 1, wherein a weight ratio of the sodium metaphosphate to the anhydrous dicalcium phosphate is from about 3:1 to about 3.2:1.

8. The anhydrous oral care composition according to claim 1, wherein a weight ratio of the sodium metaphosphate to the anhydrous dicalcium phosphate is from about 2.9:1 to about 3.1:1.

* * * * *